(12) United States Patent
Garvin

(10) Patent No.: US 6,379,338 B1
(45) Date of Patent: Apr. 30, 2002

(54) RETRACTING TIP FOR CATHETER SET

(76) Inventor: David M. Garvin, 743 Sispina Ave., Coral Gables, FL (US) 33146

( * ) Notice: Subject to any disclaimer, the term of this patent is extended or adjusted under 35 U.S.C. 154(b) by 0 days.

(21) Appl. No.: 09/679,953

(22) Filed: Oct. 4, 2000

Related U.S. Application Data

(63) Continuation-in-part of application No. 09/653,995, filed on Sep. 1, 2000, now Pat. No. 6,224,575, which is a continuation-in-part of application No. 09/620,929, filed on Jul. 21, 2000.

(51) Int. Cl.[7] .............................................. A61M 5/00
(52) U.S. Cl. ................... 604/195; 604/110; 604/164.08
(58) Field of Search ................................. 604/110, 192, 604/195, 198, 222, 223, 240, 241, 263, 164.08, 164.12

(56) References Cited

U.S. PATENT DOCUMENTS

| | | | | |
|---|---|---|---|---|
| 4,944,728 A | * | 7/1990 | Carrell et al. | 604/164.08 |
| 5,092,853 A | * | 3/1992 | Couvertier, II | 604/195 |
| 5,129,884 A | * | 7/1992 | Dysarz | 604/164.08 |
| 5,201,710 A | * | 4/1993 | Caselli | 604/110 |
| 5,681,292 A | * | 10/1997 | Tober et al. | 604/195 |

* cited by examiner

*Primary Examiner*—Anhtuan T. Nguyen
(74) *Attorney, Agent, or Firm*—McHale & Slavin

(57) ABSTRACT

A retracting tip for a catheter set has telescoping barrels and a spring loaded cannula. Telescoping of the barrels into each other releases the spring compression on the cannula and results in the cannula being withdrawn into said barrels leaving the catheter in the patient.

14 Claims, 6 Drawing Sheets

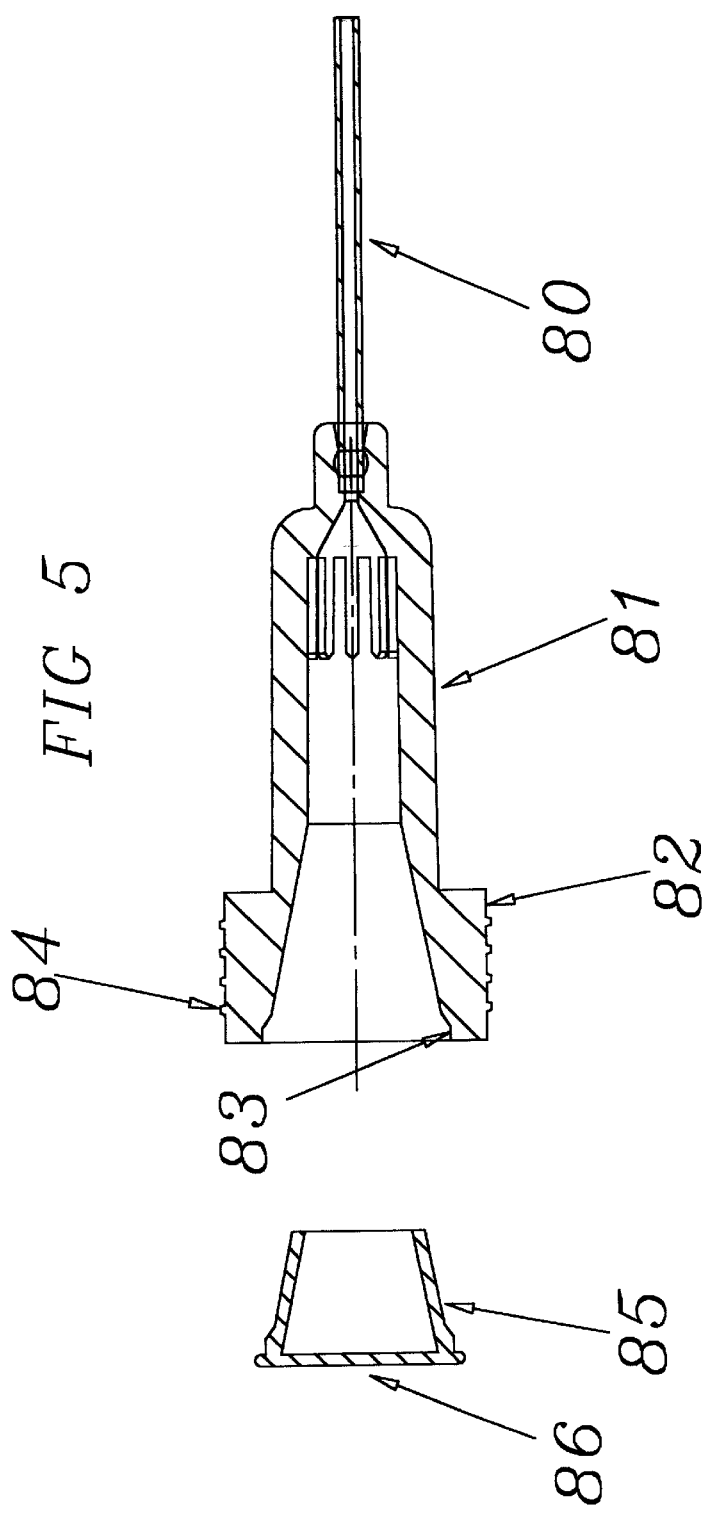
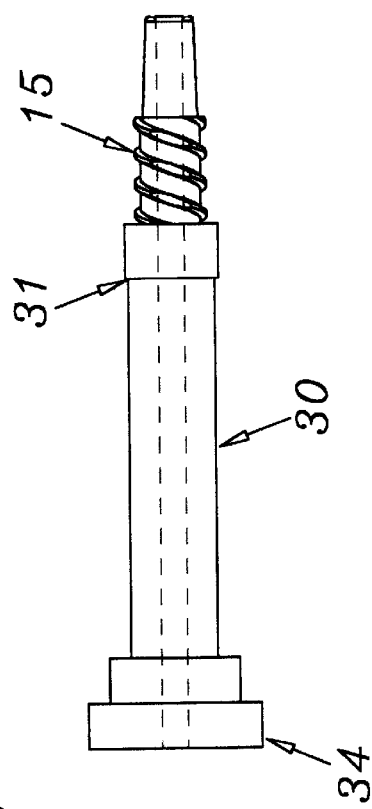
FIG 5
FIG 6

RETRACTING TIP FOR CATHETER SET

This application is a continuation in part of Ser. No. 09/653,995, filed Sept. 1, 2000 is now U.S. Pat. No. 6,224,575 which is a continuation in part of Application Ser. No. 09/620,929 filed Jul. 21, 2000. This application is related to Ser. No. 09/575,007 filed May 19, 2000 and U. S. Pat. No. 5,984,898 issued Nov. 16, 1999.

FIELD OF THE INVENTION

This invention relates generally to the collection and infusion of patient fluids, more specifically, to an assembly for coupling a catheter or other flexible tubular device with a retractable cannula/needle assembly. The retracting tip assembly includes two telescoping barrels and a collet which operate to automatically retract the needle into the interior of the barrels.

BACKGROUND OF THE INVENTION

Many medicaments and fluids are routinely infused and discharged fluids collected through a catheter system connected to the patient and an administration container or a collection container. The typical administration set has a pre-filled plastic bag or bottle connected to one end of a catheter. The catheter may be integrally formed with the bag or the bag may have a puncturable port for connection with a needle on one end of the catheter. The other end of the catheter usually has a needle/cannula for insertion into the patient intravenously or enterally.

Collection bags or containers are constructed much the same way, except that the bag or container is initially empty. To infuse or collect from a patient, the needle/cannula at the free end of the catheter is inserted through the dermal layer into the lumen of the blood vessel and taps in to the circulation system of a patient or into other parts of the body. The catheter may have a clamp or valve which is manipulated to open the passageway from the bag to the patient. Once the infusion bag is empty or the collection bag full, each may be disconnected from the patient.

Some patients may require more than one container to be used during the treatment. In such cases, a catheter or port may be placed into the body by a cannula. Initially, the cannula is inserted through the skin to the desired location then the catheter may be inserted through the cannula and the cannula is thereafter removed leaving the port and/or catheter in place. Alternatively, the catheter may be fitted over the cannula with the point of the cannula extended beyond the end of the catheter. After the cannula is inserted in the patient, it is withdrawn from the catheter leaving the catheter in place.

The retractable cannula assembly with its contaminated needle presents the danger of an inadvertent needle stick to personnel handling the used equipment. Even trace amounts of body fluids from a person with Hepatitis, Acquired Immune Deficiency Syndrome (AIDS), and other infectious diseases, transferred into another's blood stream can transmit these diseases. Thus, what is needed in the art is a needle/cannula assembly that protects from inadvertent needle sticks.

SUMMARY OF THE INVENTION

A retracting tip for a catheter set has telescoping barrels and a spring loaded cannula. Telescoping of the barrels into each other releases the spring compression on the cannula and results in the cannula being withdrawn into the barrels. The forward end of the inner barrel is telescoped into one end of a tubular outer barrel, the other end of the outer barrel has a restricted opening. The forward end of the inner barrel is formed with an enlarged circumferential ring and carries a resiliently expandable tubular collet engaging the restricted opening. The collet has a portion extending through the restricted opening of the outer barrel and that portion of the collet has an expanded dimension greater than the restricted opening. A tubular cannula holder is inserted through the collet with one end of the cannula holder extending through the collet and having a connection for removably attaching to a cannula. The cannula holder has a shoulder trap adjacent to the connection with the other end of said cannula holder disposed in the forward end of the inner barrel. The end of the cannula holder is formed with an enlarged flange. A first resilient spring is disposed in the outer barrel about said restricted opening with said spring engaging the circumferential ring of the inner barrel and urging the cannula holder toward the outer barrel. A shoulder trap on the cannula holder engages the portion of the collet thereby wedging the collet in the restricted opening. A second spring is disposed in the inner barrel about the cannula holder and engages the enlarged flange thereby urging the cannula holder into the inner barrel.

An objective of this invention is to provide a needle assembly having a catheter telescoped over the needle whereby the catheter remains in the patient after the needle is withdrawn from the patient.

An objective of the instant invention is to provide a needle assembly that causes the contaminated hypodermic cannula to retract into the assembly so that the needle is no longer exposed for accidental needle sticks. The retraction of the needle is automatically accomplished by the telescoping movement of one barrel into another barrel by activating a spring release mechanism.

It is a further objective of the instant invention to provide a retracting assembly that is attached to the cannula such that it does not interfere with the operation of the catheter set but is easily accessible for retraction of the needle.

Another objective of the instant invention is to provide a collet which expands and releases a spring biased needle retractor in response to the forward movement of the telescoping barrel. The forward end of the outer barrel carries a wedge which insures the collet fingers will spread apart upon forward movement of the collet.

A further object of this invention is to provide a catheter hub removably mounted over the collet fingers such that spreading apart of the fingers dislodges the catheter from the collet.

It is still another objective to provide an inexpensive, easily manufactured and used retracting needle assembly with a retractable needle mechanism for safe disposal and prevention of diseases.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate objects and features thereof.

BRIEF DESCRIPTION OF THE DRAWINGS

FIG. 5 is longitudinal cross sectional view of the catheter and hub of the present invention showing the resealable diaphragm for the port;

FIG. 6 is a longitudinal cross sectional view of the needle retractor; and

DETAILED DESCRIPTION

Figure 1:
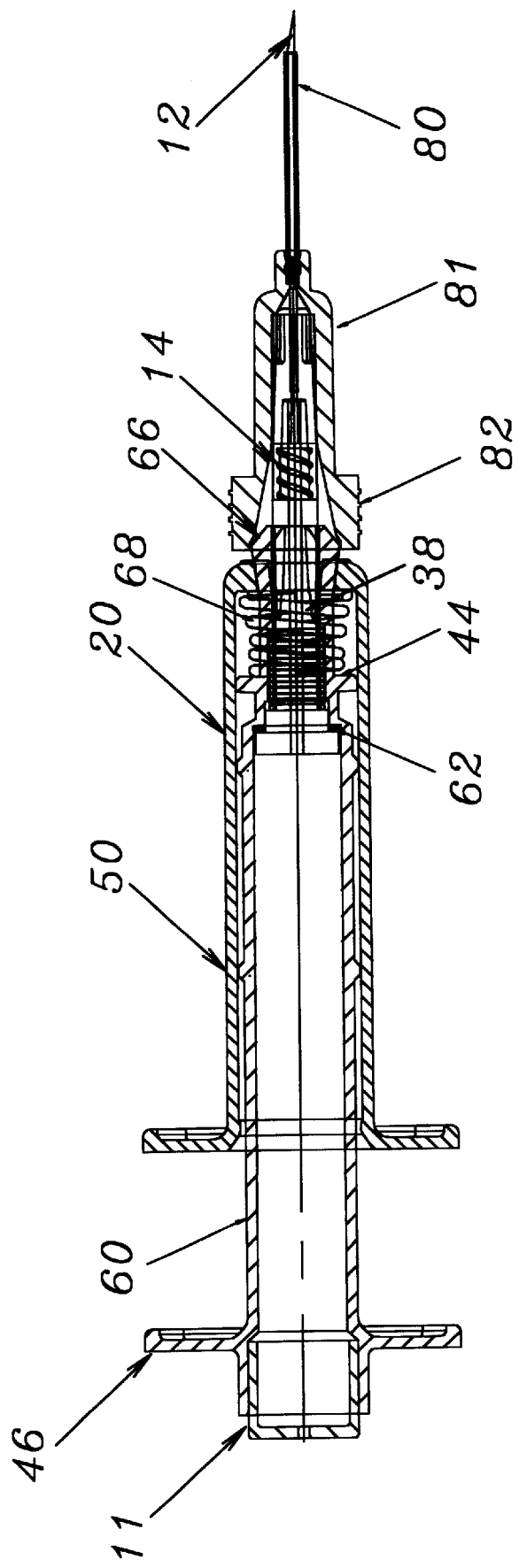
FIG. 1 is a longitudinal cross sectional view of the assembly.
Figure 2:
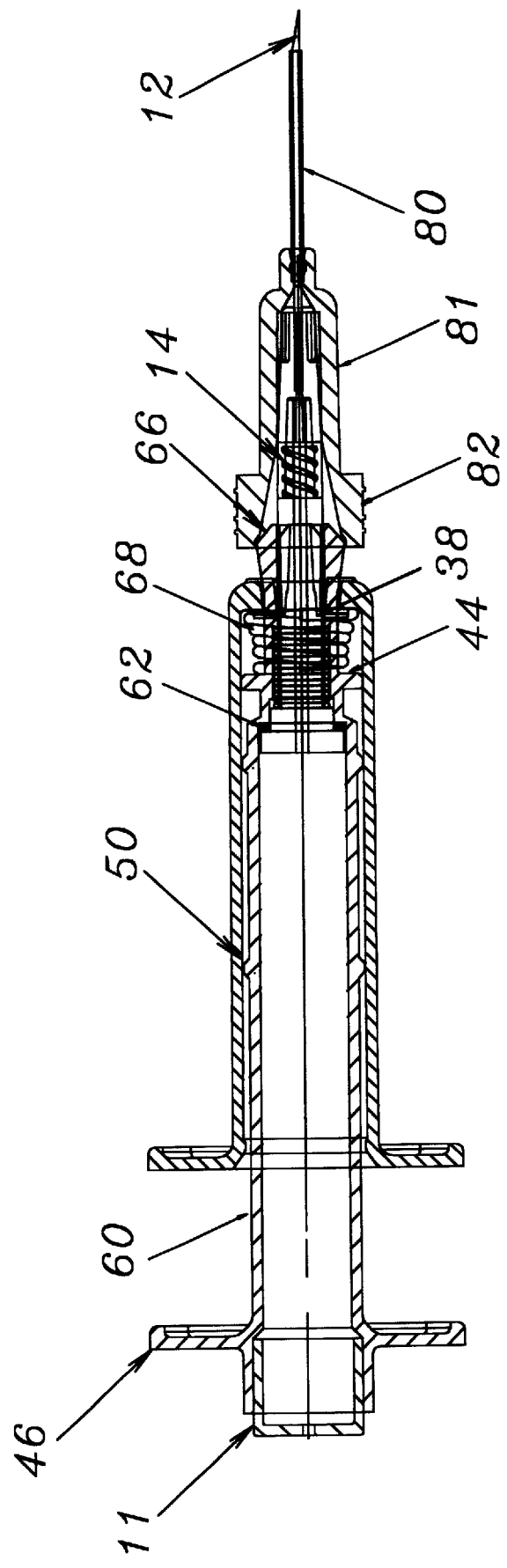
FIG. 2 is a longitudinal cross-sectional side view of the fluid collection assembly with the collet in the forward position.

As shown in FIGS. 1–2, the invention is a combination of a needle retractor and a catheter device 20. The device has a separately attached needle hub including a metal cannula 12 and a threaded attachment portion 14 cooperating with threads 15 on the needle retractor 30. This connection may also be a Leur Lok or frictional fit. Telescoped over the metal cannula 12 is a catheter 80. The catheter is a conventional flexible tube for placement in the body. The catheter 80 is connected to or integrally molded with a hub 81 and a connection port 82. The device 20 includes a hollow inner barrel 60 which cooperates with a needle retractor 30 to draw the needle 12 into the inner barrel following use of the needle. This action is accomplished by telescoping inner barrel 60 into outer barrel 50, as shown in FIG. 2. The continued stroke of the barrel 60 moves collet 66 forward and releases needle retractor 30 which is then propelled by spring action into the body of inner barrel 60 leaving catheter 80, hub 81 and port 82 in the patient.

The retracting tip assembly 20 is made up of an outer barrel or tube 50 and an inner barrel 60. The inner barrel has a forward end 64 with an enlarged circumferential ring 44 and an adjacent second circumferential ring 45, which seals the inner barrel to the inner surface of the outer barrel 50. The inner barrel 60 has an enlarged circumferential ring 44 with a central aperture 75 on the forward end. Aperture 75 is sized to accommodate the needle retractor 30. An O-ring seal 62 may be carried on the needle holder 30 to fit against the inside of inner barrel 60. At the rear end of the inner barrel 60, there is a push element 46 which is provided to engage the user's thumb.

The forward end 64 of the inner barrel 60 also includes a collet 66 which acts as a movable stop between the outer barrel and the needle retractor. The collet has slots 67 in the external funnel shape which creates a contracting and clamping effect for the collet as it is withdrawn through the opening 72 located at the forward end of the outer barrel 50. The collet is biased into a clamping or retracted position by a short spring 68 which biases the inner barrel 60 rearwardly with respect to the outer barrel 50.

The needle retractor 30, shown in detail in FIG. 6, may be a solid construction or may have a through duct into the inner barrel 60. If desired, the needle 12 may be separated from the assembly at the needle retractor 30 and an infusion bag or a collection bag connected to the needle hub. In this instance, the needle performs the function of the catheter.

Figure 3:
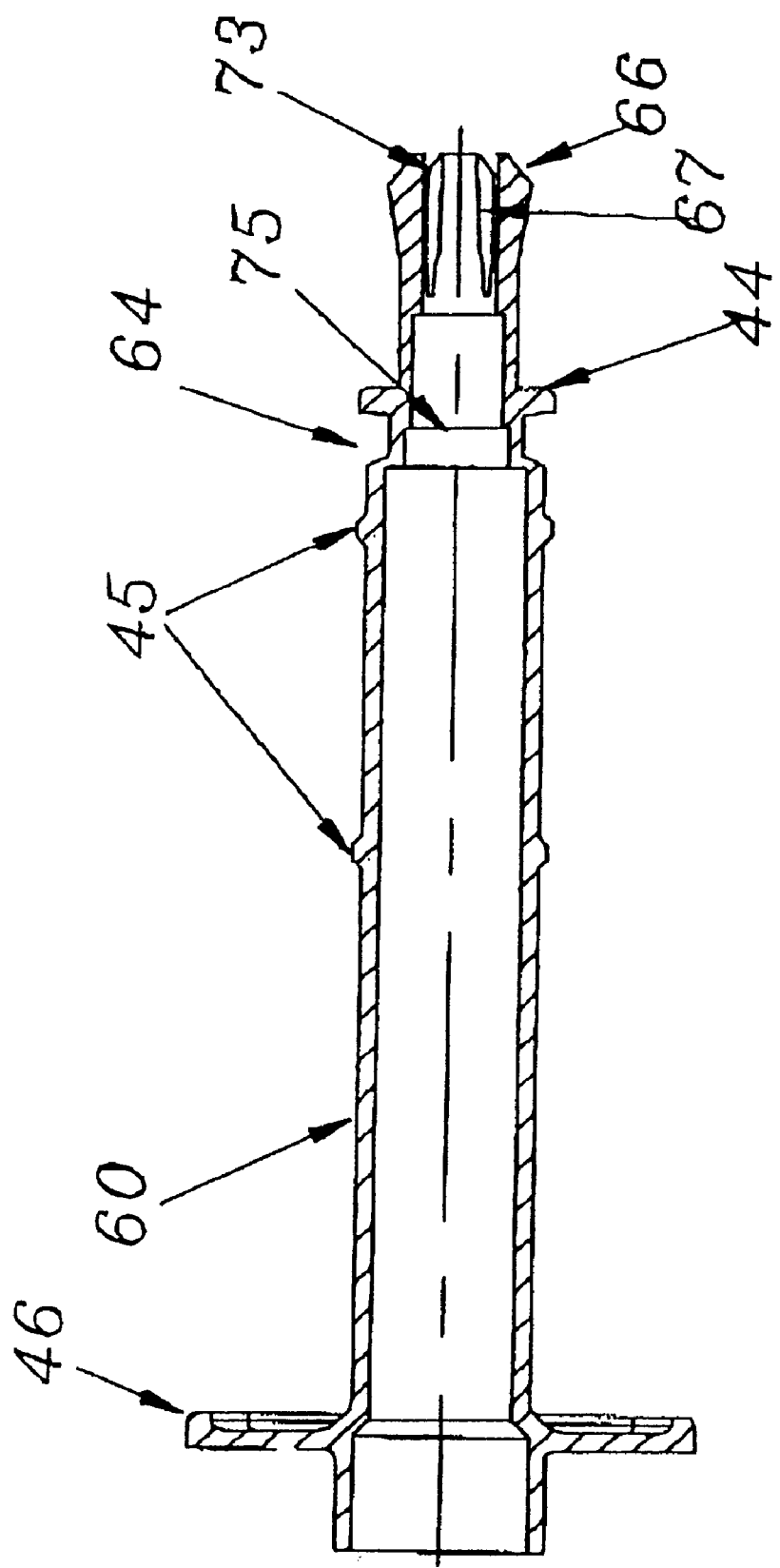
FIG. 3 is a longitudinal cross-sectional side view of the inner barrel.
Figure 4:
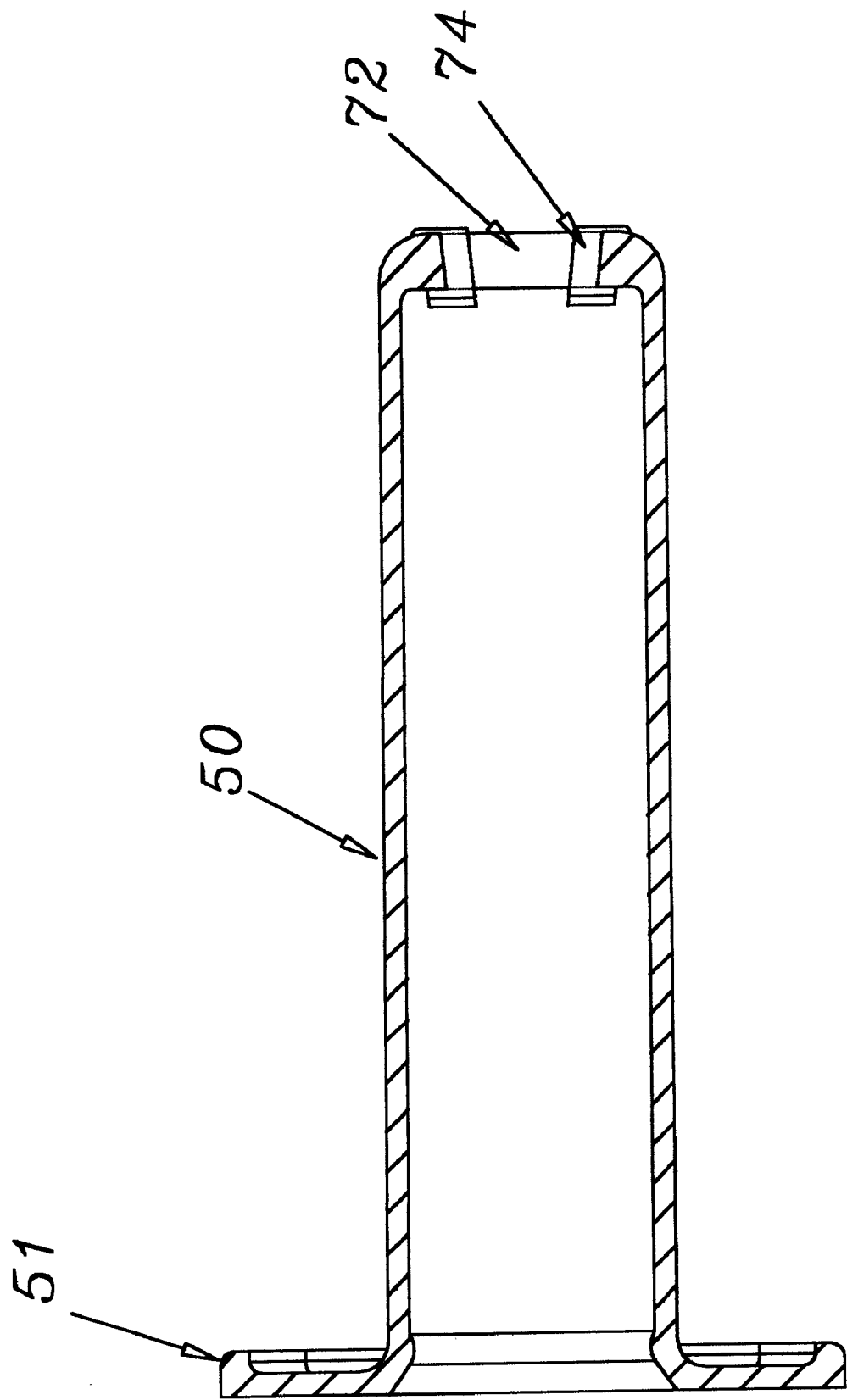
FIG. 4 is a longitudinal cross sectional view of the forward end of the outer barrel.

Details of the collet 66 of this embodiment are shown in FIG. 3. The collet includes a plurality of slots 67 which allow for expansion and contraction of the collet as the exterior funnel shape of the collet is urged forwardly and rearwardly through the forward opening 72 in outer tube 50 of the fluid collection tube holding device 20. The slots 67 are larger at the forward ends 73 of the collet and taper rearwardly. The forward ends 73 of the slots 67 are sized to accommodate the wedges 74, shown in detail in FIG. 4. When the collet 66 is urged rearwardly with respect to the outer barrel 50 by a short spring 68, the slots 67 in the collet forward end are forced into a closed position, without interference from wedges 74, reducing the diameter of the collet and clamping the holder 30. This clamping and retention of the holder are helped by the trapped edge 31 which is present of the exterior of the holder 30. The collet 66 clamps onto the holder just behind the trapped edge. The trapped edge 31 is shown as an annular element in this embodiment, however, it can take on any shape which binds against the restricting edges of the collet 66 and retains the holder 30 in the forward end of the inner barrel 60. In the closed position, the collet cooperates with the port 82 to maintain a positive friction connection. As the collet moves forward and expands, it pushes the port off the collet.

The retracting holder 30 is biased rearwardly by long spring 38 located inside the inner barrel 60. One end of the spring 38 rests against the forward wall of the inner barrel and the other end pushes on the end cap 34 of the holder. To release the holder 30, the collet 66 is expanded by forward movement of the collet 66 in response to contact with the inner barrel forward end 64 and 44. The forward movement of the collet 66 frees the collet from the constriction of the opening 72 and engages the narrowed portions 75 of the slots 67 with the wedges 74 to force the collet to expand clear of the lip on the retracting holder 30. The forward movement of the collet 66 and the spreading of the collet fingers, as shown in FIGS. 1, 2 and 5, cooperates with the inner surface 83 of the port-hub 82 to release the hub 82 from the collet 66.

Figure 7:
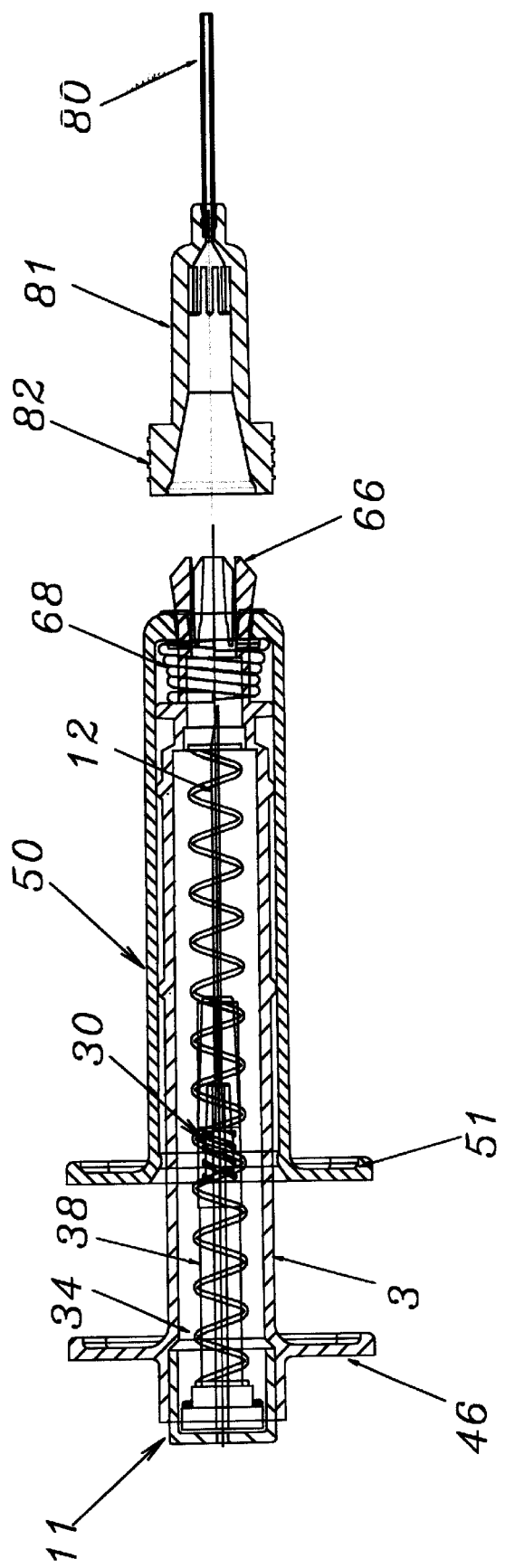
FIG. 7 is a longitudinal cross sectional view of the assembly in the retracted position with disconnected port.

As shown in FIG. 7, the shoulder trap 31 is freed from engagement with collet 66 and moves into inner barrel 60 under expansion of long spring 38 carrying cannula 12 into the assembly where it is enclosed. The contaminated cannula 12 is held in the inner barrel 60 by the expanded long spring 38.

The needle 12, shown in FIG. 2, has a bore 13 and an exterior wall sized to accept the catheter 80 without creating a binding fit. The cannula 12 must slide through the bore of the catheter 80, easily, to prevent crimping of the flexible tube when the needle is retracted.

FIG. 5 shows the catheter 80 bonded to the hub 81. In the embodiment shown, the hub is molded with the connection port 82. The connection port 82 is a conventional component produced by several medical supply manufacturers and used as a site for multiple connections to the patient. The port is sized to accommodate the forward portion of the collet 66 in the assembled configuration. The port 82 has a peripheral sloped inner shoulder 83 which removably engages the collet 66. The catheter, hub and port may be molded into one unit or may be separate components fitted together in any conventional manner, such as friction fit, adhesives or the like. After placement in the patient, the port 82 may have a resealable closure 85 inserted in the enlarged opening. The closure 85 has a diaphragm 86 to permit use of multiple sequential needles without leakage. Whether or not the port closure 85 is used depends on the configuration of the other components of the set. For example, an administration set may have a tube that is telescoped into the hub without the use of needles.

The hub also is shown with threads 84 to connect with a dosing or discharge tube, not shown, equipped with a cooperating fitting.

To use the catheter set with the retracting tip assembly, the user may insert the needle 12 and catheter 80 into the patient's body and then attach the assembly or use a preassembled cannula and assembly. In the preferred embodiment, the assembled device 20 is used to place the needle 12 and catheter 80 in the patient. Once the needle and catheter are properly placed, the operator merely grasps the device in the manner of a syringe so that inner barrel 60 and outer barrel 50 are telescoped by bringing flanges 46 and 51 together. The user pushes until the annular forward end 44 of inner barrel 60 overcomes the wedging force of spring 68 which in turn pushes the collet 66 forward. By pushing forward, as shown in FIG. 2, the collet 66 expands and the holder 30 disengages from the collet 66 and the holder 30 is propelled rearwardly into the tubular body of the inner barrel 60. Simultaneously, the expanding collet 66 disengages the port 82. The needle 12 is then disabled with the needle trapped within the assembly, as shown in FIG. 8. The catheter 80 remains in the patient's body. The catheter may then be used for long or short term treatment with various medicaments being administered and samples taken through the port without requiring additional needle sticks.

The assembly sequence of the present invention is as follows: The inner barrel 60 and the short spring 68 are loaded into the outer barrel 50 allowing the collet to extend through the restricted opening 72 and compressing the spring; the assembled holder 30 including the long spring 38 is inserted through the inner barrel and the extended collet; compression is released on the short spring by retraction of the inner barrel until the shoulder trap 31 engages the forward edge of the collet wedging the collet in the restricted opening of the outer barrel. The entire assembly includes very few polymer plastic molded parts, namely the catheter hub, port, the adapter, outer and inner barrels, the holder with metal cannula hub and two springs. By virtue of the comparatively few numbers of parts and their simplicity in execution, the present assembly and retractable needle combination can be readily and economically manufactured.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. In the combination of a catheter and a retracting cannula removably located in said catheter, said retracting cannula comprising an inner barrel telescoped into an outer barrel, the forward end of said inner barrel telescoped into one end of a tubular outer barrel, the other end of said outer barrel having a restricted opening, said forward end of said inner barrel formed with an enlarged circumferential ring and carrying a resiliently expandable tubular collet engaging said restricted opening, said collet including a portion extending through said restricted opening of said outer barrel, said portion of said collet having an expanded dimension greater than the restricted opening, a tubular cannula holder inserted through said collet, one end of said cannula holder extending through said collet and having a connection for removably attaching a cannula and catheter, said cannula holder having a shoulder trap adjacent said connection, said other end of said cannula holder disposed in said forward end of inner barrel, said other end of said cannula holder having an enlarged flange, a first resilient spring disposed in said outer barrel about said restricted opening, said spring engaging said circumferential ring of said inner barrel and urging said cannula holder toward said outer barrel, said shoulder trap engaging said portion of said collet thereby wedging said collet in said restricted opening, a second spring disposed in said collet about said cannula holder and engaging said enlarged flange thereby urging said cannula holder into said inner barrel.

2. In the combination of claim 1 wherein said connection for removably attaching said cannula and said cannula holder is a Luer-Lok.

3. In the combination of claim 1 wherein said connection for attaching said cannula and said cannula holder is in the form of screw threads.

4. In the combination of claim 1 wherein said first spring is a coil spring.

5. In the combination of claim 1 wherein said second spring is a coil spring.

6. In the combination of claim 5 wherein said first spring is a coil spring.

7. In the combination of claim 1 wherein said catheter includes an enlarged hub, said hub removably engaged with said resiliently expandable portion of said collet extending through said restricted opening of said outer barrel in the form of a friction fit.

8. In the combination of claim 7 wherein said portion of resiliently expandable tubular collet removably engaged with said hub and said hub are constructed to cooperate to disengage as said collet expands.

9. In the combination of claim 1 wherein said resiliently expandable collet has a funnel shaped exterior wall and includes slots in said wall which enable expansion and contraction of said collet.

10. In the combination of claim 9 wherein said restricted opening in said outer barrel has at least one wedge element, said wedge element disposed in said slots in said collet to force said collet to expand.

11. In the combination of claim 10 wherein said inner barrel is displaced to compress said first spring and displace said collet, said wedge element engaging said slots expanding said collet, said shoulder trap of said cannula holder disengaging said portion of said collet, said second spring resiliently expanding to displace said cannula holder through said collet into said inner barrel.

12. In the combination of claim 11 wherein said catheter includes an enlarged hub, said hub removably engaged around said collet wherein expanding of said collet disengages said hub and said collet.

13. In the combination of claim 12 wherein said disengaged hub forms a port adapted for removable connection to an administration set.

14. A method of placing a catheter and retracting cannula and safely disposing of said retracting cannula of claim 1 comprising the steps of:

a) inserting said cannula and catheter into a patient;

b) removing said cannula from the patient while leaving said catheter in said patient, c) displacing said rearward end of said inner barrel toward said one end of said outer barrel, d) compressing said spring about said restricted opening causing the displacement of said collet through said restricted opening of said outer barrel, which causes resilient expansion of said portion of said collet to disengage said shoulder trap and said catheter, resulting in expansion of said second spring driving said cannula holder into said inner barrel thereby enclosing said cannula in said inner barrel.

* * * * *